United States Patent
Matthis et al.

(10) Patent No.: US 8,870,927 B2
(45) Date of Patent: Oct. 28, 2014

(54) BONE ANCHORING DEVICE

(75) Inventors: Wilfried Matthis, Weisweil (DE); Lutz Biedermann, VS-Villingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 58 days.

(21) Appl. No.: 13/100,007

(22) Filed: May 3, 2011

(65) Prior Publication Data

US 2011/0208249 A1 Aug. 25, 2011

Related U.S. Application Data

(62) Division of application No. 11/484,180, filed on Jul. 10, 2006, now Pat. No. 7,955,359.

(60) Provisional application No. 60/698,885, filed on Jul. 12, 2005.

(30) Foreign Application Priority Data

Jul. 12, 2005 (EP) ..................................... 05015138

(51) Int. Cl.
 *A61B 17/70* (2006.01)
(52) U.S. Cl.
 CPC ......... *A61B 17/7032* (2013.01); *A61B 17/7037* (2013.01)
 USPC ...................................................... 606/270
(58) Field of Classification Search
 CPC .................. A61B 17/7032; A61B 17/7036
 USPC ........................................................ 606/306
 See application file for complete search history.

(56) References Cited

U.S. PATENT DOCUMENTS

| | | | |
|---|---|---|---|
| 5,443,467 A | 8/1995 | Biedermann et al. | |
| 5,474,551 A | 12/1995 | Finn et al. | |
| 6,063,090 A | 5/2000 | Schlapfer | |
| 6,248,105 B1 * | 6/2001 | Schlapfer et al. | 606/266 |
| 6,440,137 B1 | 8/2002 | Horvath et al. | |

(Continued)

FOREIGN PATENT DOCUMENTS

DE 20 2004 009 073 U1 9/2004

OTHER PUBLICATIONS

European Search Report for European Application No. 07001171.3 dated Feb. 22, 2007, 8 pages.

(Continued)

*Primary Examiner* — Sameh Boles
(74) *Attorney, Agent, or Firm* — Christie, Parker & Hale, LLP

(57) ABSTRACT

A bone anchoring device includes an anchoring element having a head, a receiving portion having a first region adjacent to a second end for receiving the head and a recess which is open towards a first end to form two free legs for receiving a rod. The anchoring device further includes a pressure element configured to couple to the head, a first closure element and a second closure element. The first closure element cooperates with the legs to simultaneously fix the rod in the recess and fix the head in the receiving portion, and the second closure element cooperates with the legs, the second closure element acts on the pressure element and on the rod to independently fix the head in the receiving portion and fix the rod in the recess. The first closure element and the second closure element are interchangeable.

11 Claims, 4 Drawing Sheets

(56) References Cited

U.S. PATENT DOCUMENTS

| | | |
|---|---|---|
| 6,869,433 B2 | 3/2005 | Glascott |
| 2002/0082602 A1 | 6/2002 | Biedermann et al. |
| 2003/0100896 A1 | 5/2003 | Biedermann et al. |
| 2003/0100904 A1* | 5/2003 | Biedermann ............ 606/73 |
| 2003/0125741 A1 | 7/2003 | Biedermann et al. |
| 2003/0187439 A1 | 10/2003 | Biedermann et al. |
| 2004/0181224 A1 | 9/2004 | Biedermann et al. |
| 2004/0186473 A1 | 9/2004 | Cournoyer et al. |
| 2004/0186474 A1* | 9/2004 | Matthis et al. ............ 606/61 |
| 2005/0055026 A1 | 3/2005 | Biedermann et al. |

OTHER PUBLICATIONS

European Search Report for European Application No. 05015138.0 dated Dec. 6, 2005, 7 pages.

* cited by examiner

BONE ANCHORING DEVICE

CROSS-REFERENCE TO RELATED APPLICATION(S)

This application is a divisional of application Ser. No. 11/484,180 filed Jul. 10, 2006, which claims the benefit of U.S. Provisional Application Ser. No. 60/698,885, filed Jul. 12, 2005, and claims priority from European Patent Application EP05015138, filed Jul. 12, 2005, the disclosures of which are incorporated herein by reference.

BACKGROUND

The present disclosure generally relates to devices used in bone surgery, and more particularly, relates to a bone anchoring device.

U.S. Pat. No. 5,443,467 discloses a bone screw comprising a receiver member and a screw member having a threaded portion and a head. A pressure disk is slidable within the receiver member and acts onto the head. The rod is placed on top of the pressure disk and the arrangement is locked by means of a rod locking nut and a lock nut exerting pressure onto the rod which then exerts pressure on the pressure disk, thus locking the head.

U.S. Pat. No. 6,063,090 discloses a spinal fixation system with a pedicle screw and a retainer head to connect the pedicle screw with a longitudinal support. An insert is provided with exerts a pressure onto the head of the pedicle screw which is accommodated in the retainer head. Tension means are provided to press onto the insert to lock the head of the pedicle screw in its polyaxial position and to fix the longitudinal support. Depending on the insert and the tension means the rod and the head of the bone screw may be separately fastened.

US 2003/0100896 A1 discloses an element with a shank and a holding element connected to the shank for connecting to a rod. The holding element has a recess having a U-shaped cross-section for receiving the rod with two open legs and an inner thread on the open legs and a locking element with an outer thread which cooperates with the inner thread of the legs. In one embodiment, the holding element is polyaxially connected with the head of a bone screw. To lock the head in its polyaxial position a pressure disk is provided which acts on the head when pressure is exerted onto the rod by means of an inner screw. In another embodiment the head can be locked independently from the fixation of the rod. If the two types of anchoring devices are to be used simultaneously during surgery it is necessary to have the different types of anchoring devices separately on stock or to pre-assemble the preferred anchoring device with the required pressure disk and/or the pressure element before or during surgery.

US 2004/0186473 discloses a bone anchoring device with a bone anchoring element which is polyaxially connected to a receiving portion and a pressure element to exert pressure onto the head to lock the head in its position wherein an inner screw is provided which can be screwed in the receiving portion to exert a pressure on the rod. The inner thread ends above the rod when the rod is inserted and an undercut is provided to allow a design of the receiving portion to be smaller in its dimensions.

In view of the above, there is a need for a bone anchoring device that can remedy one or more of the above described problems associated with current bone anchoring devices.

SUMMARY

According to one or more embodiments of the present disclosure, a bone anchoring device is provided that is versatile in use and compact in size. The bone anchoring device according to one or more embodiments of the present disclosure can be used with the choice of a closure element in two ways. If a single part closure element is selected, it is possible to simultaneously lock the head in its polyaxial position and to fix the rod. If a two part closure element is selected, it is possible to separately lock the head and to fix the rod. For both applications only one single receiving portion and pressure element is necessary. Therefore, the surgeon can use one bone anchoring device and can select during surgery which kind of closure mechanism shall be used.

The bone anchoring device according to one or more embodiments of the present disclosure is compact in size, since it is not necessary to use an outer nut or ring to prevent splaying of the legs. Also, the wall thickness of the receiving portion is such that there are no thinned inner portions like thread runouts or undercuts that would weaken the structure.

Further features and advantages of the disclosure will become apparent from the description of embodiments in conjunction with the accompanying drawings.

DETAILED DESCRIPTION

Figure 1:
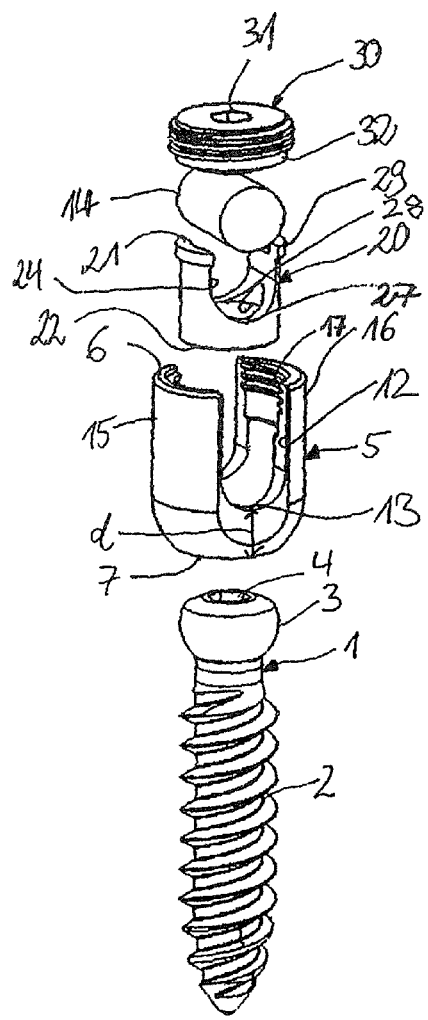
FIG. 1 shows an exploded perspective view of the bone anchoring device with a single part closure element.
Figure 2:
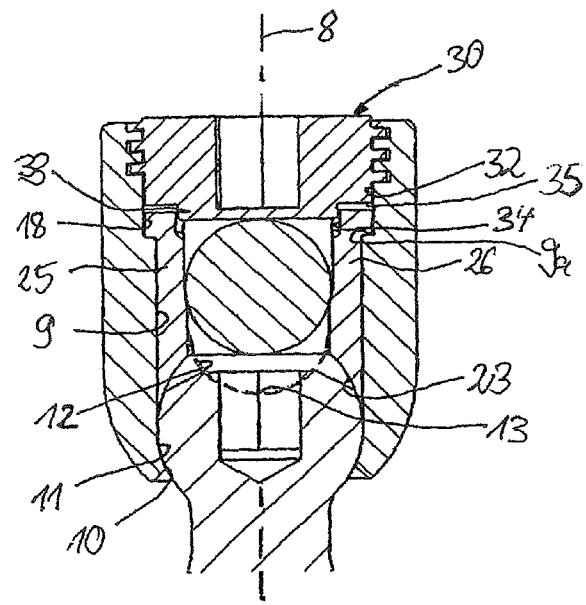
FIG. 2 shows a cross-sectional view of the bone anchoring device according to FIG. 1.
Figure 3:
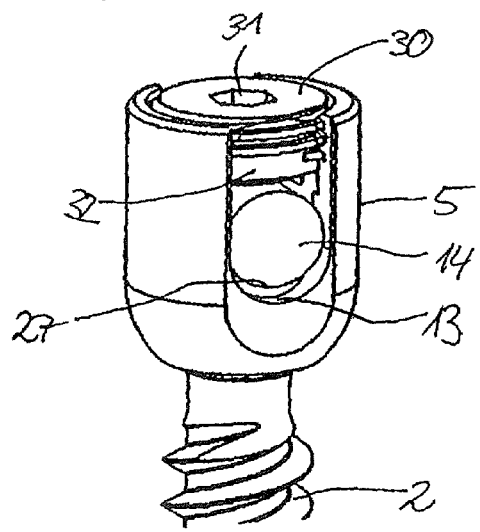
FIG. 3 shows a perspective view of the bone anchoring device of FIG. 1.

As shown in FIGS. 1 to 3 a first embodiment of the bone anchoring device of the present disclosure includes a bone screw 1 having a shank 2 with a bone thread and a spherical segment-shaped head 3 which has a recess 4 for engagement with a screwing-in tool. The bone anchoring device further includes a receiving portion 5, which is substantially cylindrical and has a first end 6 and a second end 7 opposite to the first end 6. The two ends 6, 7 are perpendicular to a longitudinal axis 8. Coaxially with the longitudinal axis 8, a first bore 9 is provided which extends from the first end 6 to a predetermined distance from the second end 7. At the second end 7, an opening 10 is provided the diameter of which is smaller than the diameter of the bore 9. The coaxial bore 9 tapers towards the opening 10. In the embodiment shown, the coaxial bore 9 tapers in form of a spherically shaped section 11. The diameter of the coaxial bore 9 can be slightly larger than the largest diameter of the head 3, so that the bone screw 1 can be guided through the bore 9 with the shank 2 extending through the opening 10 and the head 3 resting against the spherically shaped section 11.

The receiving portion 5 further has a U-shaped recess 12 which starts at the first end 6 and extends in the direction of the second end 7 so that the bottom 13 of the U-shaped recess has a distance d from the second end 7. The width of the U-shaped recess 12 in the lateral direction perpendicular to the longitudinal axis 8 can be slightly larger than the diameter of a rod 14 which is to be received in the U-shaped recess 12. By means of the U-shaped recess 12, two free legs 15, 16 are formed ending towards the first end 6. Adjacent to the first end 6, the receiving portion comprises an inner thread 17 at the legs 15, 16. A second coaxial bore 18 is provided adjacent to the first end 6 which has a diameter larger than the diameter of the first coaxial bore 9 so that a shoulder 9a is formed at the transition from the first bore 9 to the second bore 18. The inner diameter of the coaxial bore 18 and the inner diameter between opposing crests of the inner thread 17 is substantially the same. The thread 17 opens out into the U-shaped recess 12. Therefore, there is no thread runout and also no thread undercut. In an assembled state, when the rod 14 is inserted into the receiving portion 5, the inner thread 17 ends at a position at the legs 15, 16, which is above the upper surface of the rod 14.

The bone anchoring device also includes a pressure element 20, which has a substantially cylindrical construction with a first end 21 and a second end 22 opposite to the first end 21. The outer diameter of the pressure element 20 is only slightly smaller than the inner diameter of the first coaxial bore 9 to allow the pressure element 20 to be introduced into the bore 9 of the receiving portion 5 and to be moved in an axial direction. Adjacent to its second end 22 which faces the head 3 in an assembled state, the pressure element 20 comprises a spherical recess 23, the radius of which corresponds to the radius of the spherical head 3. Adjacent to its first end 21, the pressure element has a U-shaped recess 24 which extends transversely to the longitudinal axis 8. The lateral diameter of this U-shaped recess 24 is selected such that the rod 14, which is to be received in the receiving portion 5, can be inserted into the recess 24 and guided laterally therein. By means of the U-shaped recess 24, the open legs 25, 26 of the pressure element 20 are formed ending towards the first end 21. The depth of the U-shaped recess 24, as seen in the direction of the longitudinal axis 8 of the receiving portion 5 is larger than the diameter of the rod 14 to be received such that the legs 25, 26 project over the rod 14 when the rod 14 rests on the bottom 27 of the U-shaped recess 24. The pressure element 20 further comprises a coaxial bore 28 to allow for accessing the bone screw 1 with a screw driver.

As can be seen in particular from FIGS. 1 and 2, adjacent to its first end 21, the pressure element 20 includes a circumferential projection 29, the outer diameter of which is slightly smaller than the inner diameter of the second coaxial bore 18 of the receiving portion 5 in such a manner that the pressure element 20 can slide with the circumferential projection 21 in the second coaxial bore 18.

The bone anchoring device further includes a closure element which in this embodiment is a single part closure element in form of an inner screw 30. The outer thread of the inner screw 30 cooperates with the inner thread 17 provided at the legs 15,16. At one end, the inner screw 30 has a recess 31 for engagement with a screwing-in tool. At the opposite end, the inner screw 30 has a first cylindrical projection 32 the diameter of which is slightly smaller than the inner diameter of the second coaxial bore 18 such that the cylindrical projection 32 slides along the inner wall of the second coaxial bore 18 when the inner screw 30 is screwed-in between the legs 25,26. The first cylindrical projection 32 tapers into a second cylindrical projection 33 having a diameter which is larger than the diameter of the rod but smaller than the diameter of the second bore 18 and which engages in an assembled state as shown in FIG. 2 with a corresponding circular recess 34 adjacent to the first end 21 of the pressure element 20. The lower surface of the cylindrical projection 33 is flat.

The dimensions of the pressure element 20 relative to the head 3 of the bone screw and to the receiving portion 5 are such that in a state in which the bone screw is not yet locked in its final polyaxial position relative to the receiving portion 5, the bottom 27 of the U-shaped recess 24 of the pressure element 20 has a distance from the second end 7 of the receiving portion which is greater than the distance d shown in FIG. 1 so that it projects above the bottom 13 of the U-shaped recess 12 of the receiving portion 5 as shown in FIG. 3. In this state, the pressure element 20 is slidable in the first coaxial bore 9 and with its projection 21 in the second coaxial bore 18 in such a way that the projection 21 does not rest on the shoulder 9a. The dimension of the inner screw 30 in an axial direction is such that when the inner screw 30 is not yet tightened, the lower surface of the cylindrical projection 33 does not touch the surface of the rod 14.

The dimension of the inner screw 30 is such that in the finally tightened state, the inner screw 30 does not exert a pressure onto the pressure element 20, i.e., the length of the cylindrical projection 33 is such that there is a gap 35 between the surface of the first cylindrical projection 32 of the inner screw and the first end 21 of the pressure element 20. The inner thread 17 of the receiving portion 5 and the thread of the inner screw 30 is preferably a flat thread to prevent splaying of the legs 15, 16.

In use, bone screw 1 is first introduced into the receiving portion 5 with the shaft 2 guided through the opening 10 until the head 3 rests against the spherical section 11 or the edge formed by the opening 10. Then, the pressure element 20 is introduced into the receiving portion 5 such that the spherical recess 23 encompasses the upper section of the head 3 of the bone screw. In this state, the bottom 27 of the U-shaped recess of the pressure element 20 projects over the bottom 13 of the U-shaped recess 12 of the receiver portion 5. In this state, an anchoring assembly is provided by the head of the bone screw 1 being pivotably held in the spherical section 11 of the receiving portion similar to a ball and socket joint. Next, the bone screw 1 is screwed into the bone. Alternatively, the receiving portion 5, the bone screw 1 and the pressure element 20, i.e., the anchoring assembly, can be preassembled and be provided with means (not shown) preventing that the pressure element 20 falls out of the receiving portion 5.

Thereafter, the rod 14 is inserted into the receiving portion 5 such that it rests in the bottom 27 of the pressure element 20. Due to the polyaxial connection between the bone screw 1 and the receiving portion 5, the receiving portion 5 can be aligned to have the correct orientation with respect to the rod 14. Thereafter, the inner screw 30 is screwed-in between the legs 15, 16 until the lower surface of cylindrical projection 33 comes into contact with the upper surface of the rod 14. The inner wall of the second coaxial bore 18 of the receiving portion 5 acts as a guiding surface for the cylindrical projection 32 of the inner screw which prevents tilting of the inner screw at the time of screwing-in the inner screw 30.

At the same time, the second coaxial bore 18 and the shoulder 9a serve for alignment of the pressure element 20 relative to the receiving portion 5. Similarly, the circular recess 34 of the pressure element 20 forms a guiding surface for the cylindrical projection 33 of the inner screw 30.

Figures 7A, 7B:
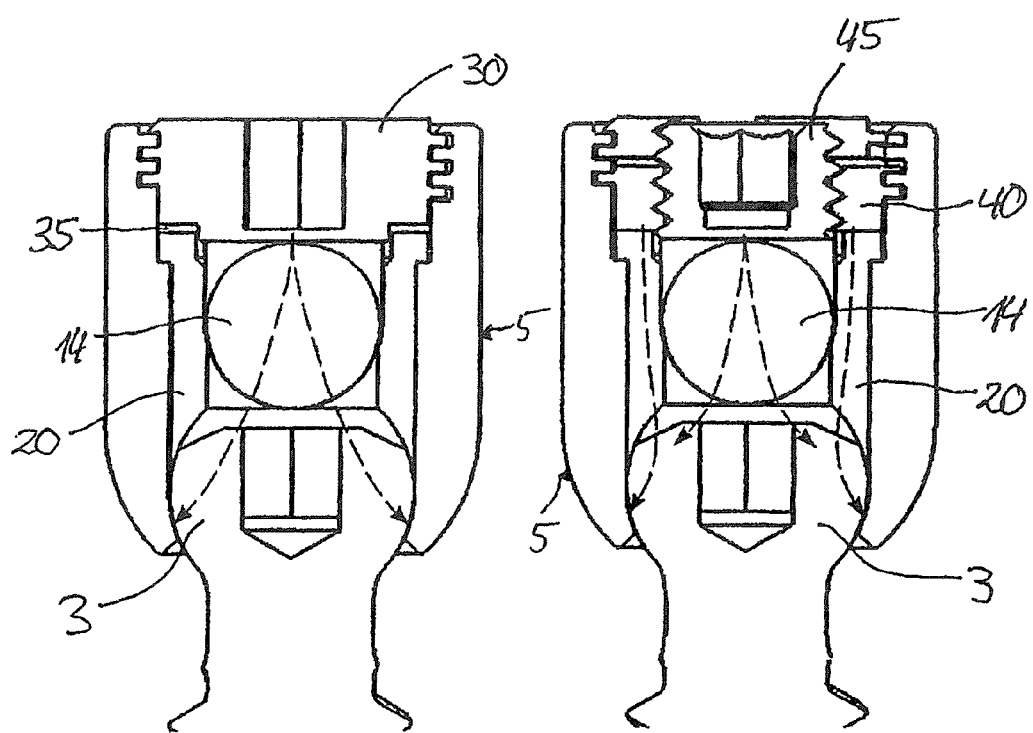
FIG. 7a shows in a schematic way the locking mechanism of the bone anchoring device with the single part closure element.
FIG. 7b shows in a schematic manner the locking mechanism of the two part closure mechanism.

As shown in FIG. 7a, at the time of final tightening of the inner screw 30, the lower surface of the inner screw 30 presses onto the rod 14 which presses onto the pressure element 20. Because of the gap 35 between the lower side of the cylindrical projection 33 and the first end 21 of the pressure element 20, pressure is exerted only on the rod 14, which itself exerts pressure on the head 3 via the pressure element 20. Thus, head 3 and rod 14 are fixed simultaneously.

The design of the receiving portion 5 is compact, since no outer securing ring or nut is necessary. Since the inner thread 17 does not have a thread runout and the inner portion of the receiving portion 5 does not have an undercut, the legs 15, 16 are stiffer because of an enhanced thickness towards the inside of the receiving portion 5. This reduces splaying of the legs 15, 16 when screwing-in the inner screw 30. Further, the pressure element 20 having the legs projecting over the rod 14 can be aligned easily in the receiving portion 5.

Figure 4:
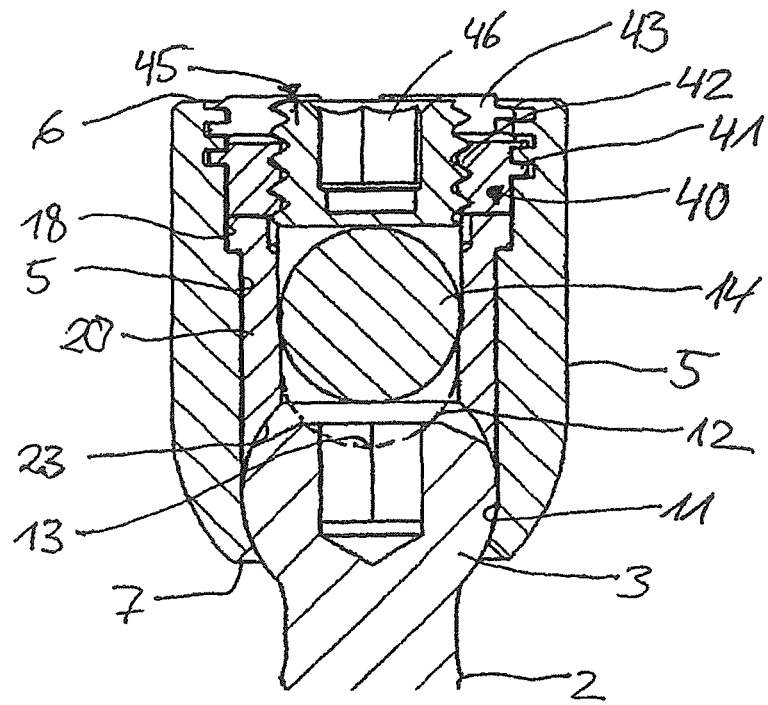
FIG. 4 shows a cross-sectional view of a bone anchoring device with a two part closure element.
Figure 5:
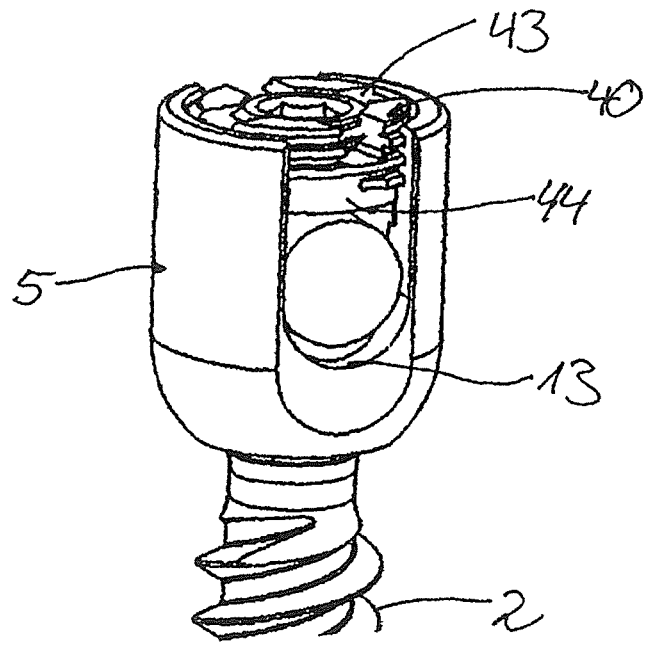
FIG. 5 shows a perspective view of the bone anchoring device of FIG. 4.

A second embodiment of the disclosure is shown in FIGS. 4, 5 and 7b. The bone anchoring device shown in FIGS. 4 and 5 differs from the bone anchoring device shown in FIGS. 1 to 3 and 7a by the closure element used. All other parts are identical and have the same reference signs, and therefore, the description thereof will be omitted.

The closure element which is part of the embodiment shown in FIGS. 4 and 5 is a two part closure element consisting of a nut 40 which can be screwed-in between the legs 15, 16 of the receiving portion 5. The nut 40 has an outer thread cooperating with the inner thread 17 of the legs 15, 16. This thread can be a flat thread to prevent splaying of the legs 15, 16. The nut 40 is further provided with an inner thread 42. On one end, slits 43 are provided for engagement with a screw driver. On its side facing the receiving portion 5, the nut 40 has an annular projection 44, the outer diameter of which is slightly smaller than the inner diameter of the second coaxial bore 18.

The closure element further comprises an inner screw or set screw 45 with an outer thread cooperating with the inner thread 42 of the nut 40. The thread can be a metric thread. The inner screw 45 has a recess 46 for engagement with a screwing-in tool. The dimension of the nut 40 is such that when it is in the fully tightened state as shown in FIG. 4, the annular projection 44 presses onto the first end 21 of the pressure element 20. The dimension of the inner screw 46 is such that it presses on the rod 14 in the fully tightened state.

In use, as in the first embodiment, first the bone screw 1 is introduced into the receiving portion 5. Then, the pressure element 20 is inserted and is first held loosely in the receiving portion 5. Alignment of the pressure element 20 is easy because of the coaxial first bore 9 and the coaxial second bore 18. Following this, the bone screw 1 is screwed into the bone and the rod 14 is inserted into the U-shaped recess 12 of the receiving portion 5, which is in alignment with the U-shaped recess 24 of the pressure element 20. At the time of placing in the rod 14, the pressure element 20 is positioned such that the bottom 27 of its U-shaped recess 24 projects over the bottom 13 of the U-shaped recess 12 of the receiving portion 5. The bone screw 1, the receiving portion 5 and the pressure element 20 can also be preassembled.

The nut 40 is then screwed-in with the inner screw 45 loosely screwed into it, until the nut 40 abuts against the upper end of the legs 25, 26 of the pressure element 20 and exerts a downward force on the pressure element 20, which presses onto the screw head 3 to lock the bone screw 1 in its final polyaxial position in the receiving part 5. In this state, the rod 14 is still slidable in the U-shaped recess 24 of the pressure element 20, since the legs 25, 26 of the pressure element 20 project over the rod 14. In addition, the rod 14 is prevented by the nut 40 from falling out or from tilting. Finally, the inner screw 45 is tightened until it presses onto the rod 14 and fixes the same. Thus, the fixing of the rod 14 takes place independently of the fixing of the head 3 as shown in FIG. 7b. As in the first embodiment, the bone anchoring device is compact since an outer securing element is not needed. Further, an alignment of the pressure element is facilitated.

Figure 6:
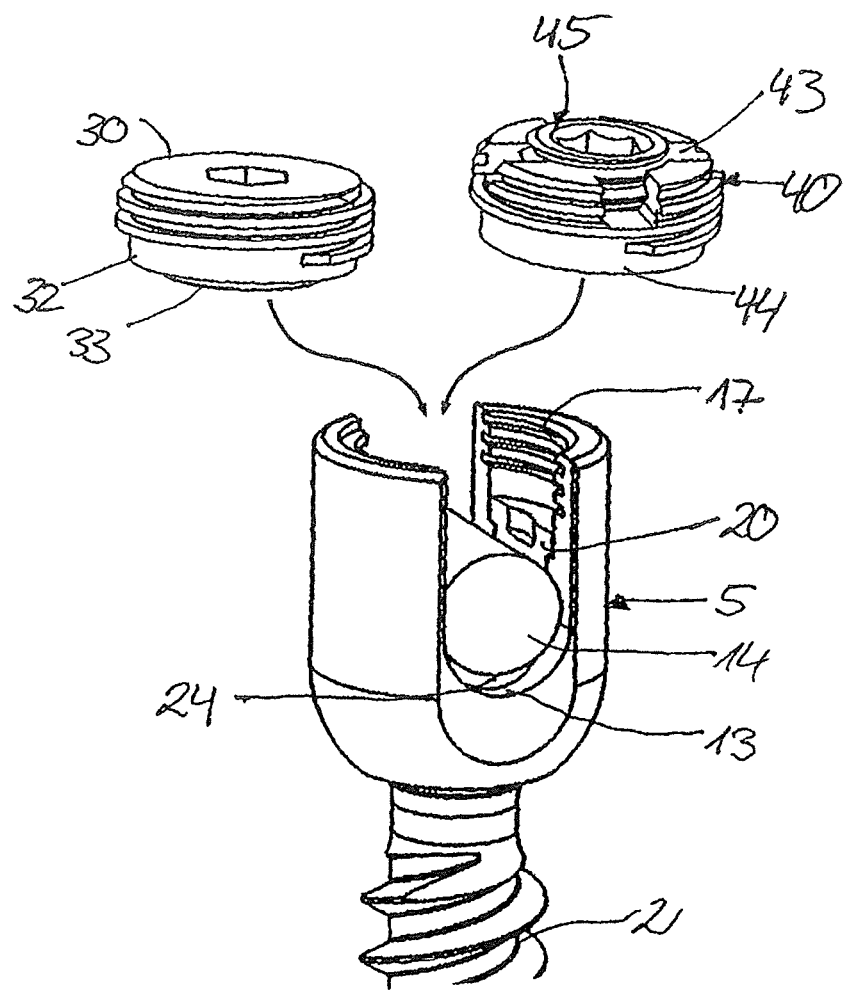
FIG. 6 shows possibilities of use of the bone anchoring device with a single part closure element and a two part closure element.

As shown in FIG. 6, during surgery, a surgeon can select whether a single part closure element 30 or a two part closure element 40, 45 is to be used in conjunction with the same bone anchoring device. For certain applications, a single part closure element with simultaneous locking of the head 3 and fixation of the rod 14 may be advantageous in particular if the fixation has to take place rapidly. For certain other applications, it may be advantageous to have the separate fixation of the head 3 and the rod 14. Since the surgeon can use the same bone anchoring device and is free to select the desired closure element, it is not necessary to have different receiving portions with different pressure elements or different bone anchoring devices available.

Modifications of the embodiments of the present bone anchoring device are possible. Instead of a flat thread, other thread forms can be used. This may require an additional outer securing element (not shown), such as a ring or a nut cooperating with an outer thread of the legs. It is also conceivable to omit the inner thread and instead use a cap (not shown) with a securing pin (not shown) pressing onto the rod 14. In this case, the pin should be shaped such that it does not press onto the first end 21 of the pressure element 20 when it touches the rod 14.

The spherically-shaped section 11 of the receiving portion 5 against which the head 3 rests needs not to be spherically shaped, but can have any other shape as long as the head 3 is held by the edge of the opening 10 like a ball and socket joint.

Further modifications are possible. In the second embodiment, the nut 40 may have an additional cap portion (not shown) at its end facing away from the cylindrical projection 44 to eliminate any danger of splaying of the legs 15, 16. In addition, modifications similar to that of the first embodiment are conceivable. In a further modification, the receiving portion 5 is designed so as to allow the introduction of the head 3 from the bottom of the receiving portion 5, that is, from the second end.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A bone anchoring device comprising:
an anchoring element comprising a shank to be anchored to a bone or a vertebra and a head;
a rod;
a receiving portion comprising a first end and a second end opposite to the first end, a longitudinal axis passing through the two ends, a bore coaxial with the longitudinal axis, a first region adjacent to the second end for receiving said head and a recess which is opened towards the first end and which forms two free legs for receiving the rod;
a pressure element to exert a pressure on said head to lock said head in the receiving portion, wherein said pressure element has a first end and a second end opposite to the first end and a U-shaped recess which is open towards the first end to receive the rod, the depth of the U-shaped recess being larger than the diameter of the rod;
a one-piece closure element configured to engage with said legs to simultaneously fix the rod in said recess of the pressure element and fix said receiving portion to the head; and
wherein an inner thread is provided at said legs and said closure element is an inner screw and wherein, when the bone anchoring device is assembled, the closure element is screwed-in between said legs and exerts a pressure directly on said rod, but not directly on said pressure element, to simultaneously fix the rod in said recess of the pressure element and fix said receiving portion to the head.

2. The bone anchoring element of claim 1, wherein said closure element comprises a projection which contacts the rod.

3. The bone anchoring device of claim 2, wherein the projection has a length that is selected such that there is a gap in the longitudinal direction between the pressure element and the closure element when the rod is fixed.

4. The bone anchoring device of claim 1, wherein said closure element comprises a central projection acting on said rod, the length of the central projection being selected such that there is a gap between the pressure element and the closure element when the rod is fixed.

5. The bone anchoring device of claim 4, wherein a sum of the length of said projection and a diameter of the rod is greater than a height of the pressure element from the bottom of the recess of the pressure element to the first end of the pressure element.

6. The bone anchoring device of claim 1, wherein the inner thread ends above said rod when the rod is inserted in the recess of the pressure element, and wherein adjacent to the inner thread, a guiding surface is provided for guiding the insertion of the closure element.

7. The bone anchoring device of claim 1, wherein a maximum inner diameter of the receiving portion is not larger than a diameter between opposing crests of said inner thread.

8. The bone anchoring device of claim 1, wherein said recess in the receiving portion is substantially U-shaped.

9. The bone anchoring device of claim 1, wherein said recess of said pressure element is substantially U-shaped.

10. The bone anchoring device of claim 1, wherein the inner thread opens out into the recess.

11. A bone anchoring device comprising:

an anchoring element comprising a shank to be anchored to a bone or a vertebra and a head;

a rod;

a receiving portion comprising a first end and a second end opposite to the first end, a longitudinal axis passing through the two ends, a bore coaxial with the longitudinal axis, a first region adjacent to the second end for receiving said head and a recess which is opened towards the first end and which forms two free legs for receiving the rod;

a pressure element to exert a pressure on said head to lock said head in the receiving portion, wherein said pressure element has a first end and a second end opposite to the first end and a recess which is open towards the first end to receive the rod, the depth of the recess being larger than the diameter of the rod;

a one-piece closure element configured to engage with said legs to simultaneously fix the rod in said recess of the pressure element and fix said receiving portion to the head; and wherein said closure element comprises a projection that, when assembled to the receiving portion, extends into the recess of the pressure element and contacts the rod to simultaneously fix the rod in said recess of the pressure element and fix said receiving portion to the head.

* * * * *